(12) United States Patent
McAfee et al.

(10) Patent No.: US 6,510,743 B2
(45) Date of Patent: Jan. 28, 2003

(54) REUSABLE IN SITU CONCRETE TEST SPECIMEN APPARATUS AND METHOD

(76) Inventors: Ralph Glenn McAfee, 4265 Ray Dr., La Plata, MD (US) 20646; Robert E. Carpenter, Jr., 3001 Fox Den La., Oakton, VA (US) 22124

( * ) Notice: Subject to any disclaimer, the term of this patent is extended or adjusted under 35 U.S.C. 154(b) by 0 days.

(21) Appl. No.: 09/816,106

(22) Filed: Mar. 26, 2001

(65) Prior Publication Data

US 2001/0035053 A1 Nov. 1, 2001

Related U.S. Application Data

(60) Provisional application No. 60/197,009, filed on Apr. 13, 2000.

(51) Int. Cl.$^7$ ................................................. G01N 3/00
(52) U.S. Cl. ......................................................... 73/803
(58) Field of Search .................. 73/802, 803; 405/223, 405/50; 106/707, 644; 428/317.9, 294.7; 264/71

(56) References Cited

U.S. PATENT DOCUMENTS

| | | |
|---|---|---|
| 3,176,053 A | 3/1965 | Distasio |
| 3,541,845 A | 11/1970 | Kierkegaard-Hansen |
| 3,595,072 A | 7/1971 | Richards |
| 3,861,201 A | 1/1975 | Kaindl |
| 3,974,679 A | 8/1976 | Nasser |
| 4,182,191 A | 1/1980 | Ikeda |
| 4,425,801 A | 1/1984 | Stoll |
| 4,501,153 A | 2/1985 | Mehes et al. |
| 4,588,443 A * | 5/1986 | Bache ........................ 106/97 |
| 5,677,495 A | 10/1997 | Johnson et al. |
| 6,343,894 B1 * | 2/2002 | Fearn ........................ 405/233 |

FOREIGN PATENT DOCUMENTS

GB  1413160  11/1975

OTHER PUBLICATIONS

American Society for Testing and Materials, Designation C873–94, "Standard Test Method for Compressive Strength of Concrete Cylinders Cast in Place in Cylindrical Molds," May 1994.

* cited by examiner

*Primary Examiner*—Max Noori
(74) *Attorney, Agent, or Firm*—Richard C. Litman

(57) ABSTRACT

A reusable apparatus for forming in situ concrete test specimens comprises a flexible open outer container and a series of smaller closable cylinders for placement within the larger container. The assembly is placed within a depression formed in the wet concrete when the slab is poured, with outer and inner containers being filled with representative concrete of the slab. The assembly is left for the concrete to cure, with smaller containers removed from the larger container after curing. Apparatus is included for facilitating lifting the sample from the slab, after curing. The larger portion of surrounding concrete is then broken away to access the smaller cylinders, which may be shipped to a testing facility where the inexpensive containers are removed to expose the test specimens. The larger outer container may be flexed to remove it from the depression, and the depression filled with fresh concrete to repair the test site.

19 Claims, 7 Drawing Sheets

REUSABLE IN SITU CONCRETE TEST SPECIMEN APPARATUS AND METHOD

CROSS-REFERENCE TO RELATED APPLICATION

This application claims the benefit of U.S. Provisional Patent Application Ser. No. 60/197,009, filed Apr. 13, 2000.

BACKGROUND OF THE INVENTION

1. FIELD OF THE INVENTION

The present invention relates generally to equipment and methods for testing material specimens, and more specifically to an apparatus and method for forming concrete specimens for comprehensive strength testing of ACI (American Concrete Institute) "field cured" cylinders. These cylinders are used primarily to insure proper concrete curing for the initiation of early form work removal (i. e., stripping of forms) during construction. The present equipment or apparatus is set into the concrete being poured, and forms a plurality of specimen cylinders meeting the requirements for ASTM testing. The test specimens formed by the present apparatus and method cure in situ, thus providing accurate and representative specimens of the remainder of the concrete from which the specimens were taken. Nearly all of the present apparatus is reusable, thus cutting testing expenses considerably.

2. DESCRIPTION OF THE RELATED ART

It is a standard practice in the construction industry, to test samples of various materials used during construction. This is especially true of concrete, where many field cured specimens are generally required when structural concrete is poured. These specimens are taken from a number of locations across the element or slab when it is poured.

The testing of such specimens is such a standard practice, and so regulated, that the American Society for Testing and Materials (ASTM) has developed certain criteria for the formation and testing of such concrete test specimens. One of the most critical criterion is that the field cured test specimens represent accurate samples of the cured concrete slab. This is critical, as concrete is exothermic (i. e., gives off heat) as it is curing, due to the heat of the hydration reaction which occurs. Accordingly, ASTM requires that field cured specimens which are cast separately from the slab, be treated during curing to closely approximate the heat developed during the curing process in the more massive slab. If the specimens are not in situ, this is difficult to achieve. Also, the specimens must be kept moist until the cure is complete, just as in the case of the poured slab. Any significant variation in the procedure can result in the specimens being an inaccurate representation of the actual qualities of the cast slab they are supposed to represent.

Accordingly, a need will be seen for a means of providing in situ concrete test specimens by means of a largely reusable apparatus. The only portion of the apparatus which is not reusable, comprises an inexpensive plastic cylinder in which the test specimens are cast. The remainder of the device, including the larger container used to encapsulate the smaller test specimen containers during pouring and curing, is removable from the poured slab or foundation after curing. Yet, the sample cylinders formed by means of the present apparatus, are surrounded by the concrete slab during the cure and receive the same heat from the exothermic reaction as does the remainder of the concrete in the slab. The result is a very accurate representation of the actual condition of the concrete of the cured slab, with the largely reusable apparatus resulting in relatively low costs for the test specimens. A method of forming such test specimens in accordance with the apparatus of the present invention, is also disclosed.

A discussion of the related art of which the present inventor is aware, and its differences and distinctions from the present invention, is provided below.

U.S. Pat. No. 3,176,053 issued on Mar. 30, 1965 to Joseph R. Di Stasio, titled "Method For Obtaining Test Cores," describes an apparatus much like that described in ASTM C873-94, in which outer and inner cylinders are set in the concrete slab at the time of pouring the slab. The outer cylinder remains in place in the concrete after it cures, with the single inner cylinder and its specimen being removed from the outer cylinder. Di Stasio describes his outer cylinder as being formed of materials such as galvanized sheet steel or plastic, and while a very few such cylinders would not add appreciably to the cost of a project, a very large poured concrete project could require thousands of specimens spread throughout the slab. Leaving a major part of the test apparatus buried in the concrete in such a situation where thousands of tests may be required, obviously adds considerably to the cost of the project. Moreover, it is noted that Di Stasio configures his outer and inner containers to leave an air gap between the two. The inner container is thus somewhat insulated from the larger exterior mass of concrete, and the heat of its hydration reaction. The present apparatus and method does not provide any air gaps between the concrete slab and the test specimen apparatus, thus providing a more representative cure and a more accurate specimen.

U.S. Pat. No. 3,541,845 issued on Nov. 24, 1970 to Peter Kierkegaard-Hansen, titled "Method For Testing The Strength Of The Material Of Cast Structures, Particularly Concrete Structures," describes a reusable test device in which a portion of the device is cast into the concrete and a tension rod is threaded into the device through a hole formed in the concrete. The rod is used to apply tension to the part which is cast into the concrete, until the assembly breaks loose. The tensile force required to break the cast-in part loose, indicates the strength of the concrete. This test method is opposite that described in ASTM C873-94 and the present disclosure, in which compressive force is applied to a specimen removed from the slab after curing.

U.S. Pat. No. 3,595,072 issued on Jul. 27, 1971 to Owen Richards, titled "Concrete Testing Means," describes another tensile testing method and apparatus, similar to that of the Kierkegaard-Hansen U.S. Patent discussed immediately above. Richards uses a hydraulically actuated tension device to pull a rod which has been threaded into an anchor device in the concrete. While the entire apparatus is recoverable from the concrete (assuming the test is continued to destruction), the tensile test is not in accordance with ASTM methods for compressively testing specimens removed from a concrete slab, whereas the present invention provides a means for forming specimens which are accurate representations of the remainder of the concrete slab and which comply dimensionally with current ASTM test equipment.

U.S. Pat. No. 3,861,201 issued on Jan. 21, 1975 to Franz Kaindl, titled "Method And Apparatus For Early Strength Testing Of In-Place Concrete," describes the use of a screen installed before the concrete is poured, for screening large aggregate pieces in order to provide a more uniform specimen. A base may be imbedded in the concrete into which a tension rod is installed for tensile strength testing, or the specimen may be compressively tested in place as desired.

The test specimen is not cast in place and then removed for testing, as provided by the present invention. While the goal of the Kaindl apparatus, i.e., to provide a uniform representative specimen free of large aggregate pieces which would produce large variation in the results, is appreciated, the test resulting from the Kandl device may not be truly representative.

U.S. Pat. No. 3,974,679 issued on Aug. 17, 1976 to Karim W. Nasser, titled "Accelerated Concrete Strength Testing," describes a testing apparatus which applies pressure and heat to a cylinder(s) of wet concrete. The heating and pressure result in a cure equivalent to a 28 day aging period, in a time of only about five hours. The apparatus is quite complex and costly in comparison to the present in situ specimen apparatus, and in any event, some of the wet concrete mix of the slab being poured must be placed in the mold(s) of the Nasser apparatus in order to have a truly representative sample. Thus, the Nasser apparatus must be located on, or very near, the actual job site; this would appear to pose some problems regarding portability and operation. The present in situ specimen apparatus is placed directly in the slab being poured, with the contents curing with the remainder of the slab, to provide accurate specimens of the concrete slab.

U.S. Pat. No. 4,182,191 issued on Jan. 8, 1980 to Shoji Ikeda, titled "Method Of Immediate Estimation Of Compressive Strength Of Concrete Through Quick Hardening," describes the addition of an alkali hydroxide and an alkali accelerator to the wet mix to accelerate the curing and aging chemically. The resulting specimen is not chemically identical to the concrete of the poured slab, due to the alkali hydroxide and accelerator additions, whereas the present invention uses exactly the same concrete as used in the rest of that area of the slab. Moreover, the Ikeda process requires that the specimen be poured separately from the slab, rather than poured in situ, as in the present system.

U.S. Pat. No. 4,425,801 issued on Jan. 17, 1984 to Ulrich W. Stoll, titled "Device And Procedure For Measuring In Situ Strength Of Concrete And The Like," describes a device imbedded in the fresh concrete at the time it is poured. After curing, a torque is applied to a handle extending from the device, with the breakaway force being used to determine the strength of the concrete. Thus, the Stoll device and method relate more to the actual testing of the concrete, rather than to any provision for the formation of test slugs or specimens, as in the present invention. In any event, the Stoll apparatus applies a torque to the test sample, rather than a conventional compression test in accordance with standard ASTM procedures.

U.S. Pat. No. 4,501,153 issued on Feb. 26, 1985 to Ferenc Mehes et al., titled "Test Machine For Determining Concrete Strength," describes a device having a hollow conical section which is imbedded in the wet concrete. After curing, a tensile force is applied to the device, with the separation line occurring across the narrower lower end of the device when the breaking point is reached. Thus, the Mehes et al. device actually tests the concrete in situ, rather than providing an in situ test specimen for testing using a conventional remotely located ASTM test apparatus, as provided by the present invention. The present apparatus and method provides test specimens which are fully compatible with conventional and accepted ASTM compressive testing machines and procedures, unlike the Mehes et al. device.

U.S. Pat. No. 5,677,495 issued on Oct. 14, 1997 to Claude D. Johnson et al., titled "Compressive Strength Testing Of HPC Cylinders Using Confined Caps," describes the provision of caps specially formed for use in testing high performance concrete (HPC). Conventionally, cylindrical concrete specimens are tested under compression to determine their ultimate compressive breaking strength. Caps are placed upon each end of the concrete cylinder, to distribute the compressive forces more uniformly across the ends of the cylinder and reduce splitting or shattering of the edges of the cylinder before maximum compressive pressure is reached. Thus, the Johnson et al. U.S. Patent is directed more to the actual testing of concrete specimens, rather than the forming of such specimens in situ in a reusable apparatus, as is accomplished by the present invention.

British Patent Publication No. 1,413,160 published on Nov. 5, 1975 to Shell International Research Maatschappij B. V., titled "Method And Means For Load Testing Open-Ended Piles Penetrating The Soil," describes a method and apparatus for testing the solidity of hollow pilings driven into the ground. A compressive force is applied to a plate at the bottom of the piling, and bears against an upper plate anchored within the piling. Shifting of either the lower plate or the piling indicates some instability. Thus, the '160 British Patent Publication does not disclose any means of providing an in situ concrete specimen for testing, but rather discloses an in situ test for the anchoring of a piling in the soil, unlike the present invention.

Finally, the American Society for Testing and Materials (ASTM) document no. C873-94, titled "Standard Test Method For Compressive Strength Of Concrete Cylinders Cast In Place In Cylindrical Molds," describes such a test method in which a cylindrical shell is permanently imbedded in the wet concrete, with a separate cylindrical container installed within the outer shell. Concrete is poured in and around the assembly and allowed to cure. The inner shell containing the single cured specimen is then removed from the imbedded outer shell after the concrete has cured, and transported for testing. The problem with this ASTM apparatus and process has been noted above, in that standard procedures may require a large number of separate test specimens from a relatively large slab. The large number of outer cylinders which must be left imbedded in the concrete, result in a significantly higher cost for the project. The present apparatus and method recovers everything from the slab, with only a few very inexpensive molds destroyed to recover the specimens cast therein. Moreover, the ASTM procedure is silent regarding any capping or closure of the removed mold, whereas the present apparatus includes caps which are applied to the individual molds in order to retain moisture and protect the specimens until testing. Also, the present apparatus preferably includes a plurality of separate molds in each larger reusable shell or container, thus providing a series of specimens to insure the consistency of the compressive strength results. The present apparatus preferably provides three test cylinders, while only two are required by ASTM and ACI. By providing three test cylinders, any wide variation which appears during the testing can be dealt with. As an example, if the three specimens provided by the present sample apparatus test at 3550 psi, 3520 psi, and 2220 psi, one can be reasonably certain that the actual compressive strength is slightly over 3500 psi, with the low test being an obvious anomaly which may be discarded. By using an average of three specimens from each test point, such variations will show which are not at all apparent if only two samples are taken and one of those specimens produces an anomalous result; the sample producing the erroneous result cannot be determined with only two specimens.

None of the above inventions and patents, either singly or in combination, is seen to describe the instant invention as claimed.

SUMMARY OF THE INVENTION

The present invention comprises a reusable, in situ concrete test specimen apparatus, and method for using the apparatus and forming test specimens. The present apparatus essentially includes a relatively large and flexible open outer container which is placed within the area where a concrete slab is to be poured. A series of smaller closable containers is placed within the larger container. The smaller containers rest upon a platform or base which may be lifted from the larger container (along with all cured concrete therein) once the concrete has cured. The smaller containers are filled with the same concrete mix as used to form the remainder of the slab at least in the immediate area, and thus serve as representative specimens of the concrete placed in the slab.

The smaller containers remain capped after the concrete is poured to retain the moisture in the containers for proper curing of the specimens. As the specimens cure in situ, they are subject to the same latent heat developed by the exothermic reaction of the remainder of the slab during cure, and need not be heated by other means. Once the concrete is cured and the specimens removed, the outer flexible container may be removed from the resulting hole, and the hole filled with concrete to close the test void in the slab. The present apparatus is completely reusable, excepting the inexpensive smaller cylindrical containers which are cut away from the cured specimens contained therein for testing those specimens. Thus, the present test specimen forming apparatus and method provides considerable economic advantages over other earlier methods and devices.

Accordingly, it is a principal object of the invention to provide an improved reusable apparatus for forming concrete test specimens in situ, and a method of forming such specimens in situ using the present apparatus.

It is another object of the invention to provide an improved apparatus for forming concrete test specimens, comprising a relatively larger, flexible, open outer container and series of smaller closable containers for placing in an area where a concrete slab is being poured, for filling with a representative specimen of the poured concrete.

It is a further object of the invention to provide an improved apparatus for forming concrete test specimens including means for removing the smaller containers from the larger container after the concrete poured therein has cured.

An additional object of the invention is to provide an improved apparatus for forming concrete test specimens which smaller containers may remain sealed until delivered for testing, and which smaller containers form specimens which are dimensionally acceptable for standard ASTM compressive test equipment and procedures.

Still another object of the invention is to provide an improved apparatus for forming concrete test specimens which larger outer container is removable from the concrete after removal of the smaller containers therefrom.

It is an object of the invention to provide improved elements and arrangements thereof in an apparatus for the purposes described which is inexpensive, dependable and fully effective in accomplishing its intended purposes.

These and other objects of the present invention will become apparent upon review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention comprises a reusable apparatus for in situ forming of concrete test specimens and method of forming such specimens using the present apparatus, wherein nearly all of the apparatus is removable from the concrete slab after the concrete has cured. The reusability of the present apparatus provides significant cost savings to a contractor or builder who has occasion to pour a large amount of concrete, as generally a relatively large number of test samples must be provided in accordance with American Society for Testing and Materials (ASTM) standards. With conventional apparatus for forming test specimens, most of the apparatus was left in the cured concrete slab, thus resulting in considerable expense in unrecoverable equipment.

Figure 1:
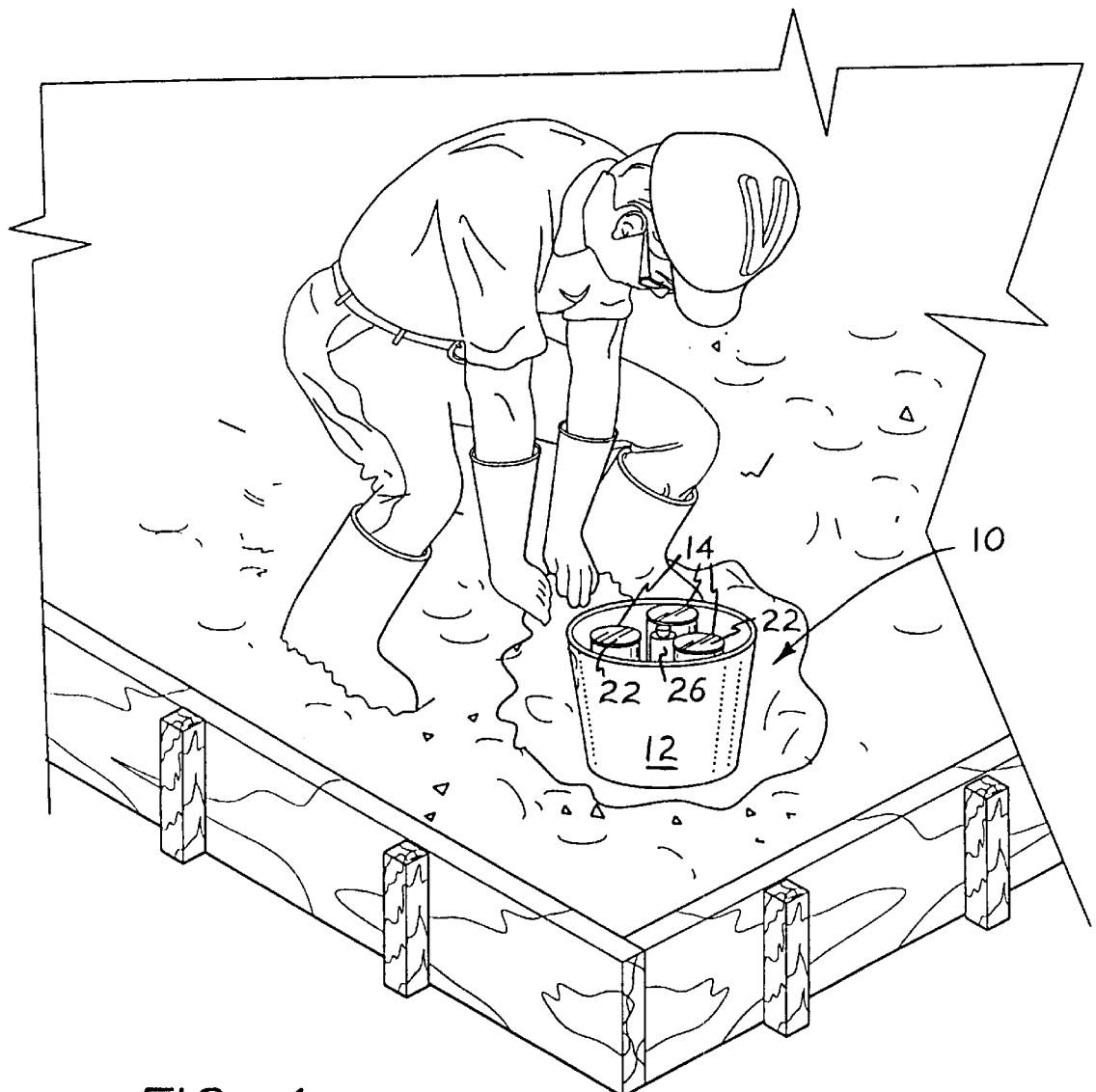
FIG. 1 is an environmental perspective view of the present in situ concrete test specimen forming apparatus being placed within a depression formed in a freshly poured slab of wet concrete and readied for filling with like concrete.

FIG. 1 provides an environmental perspective view of the present apparatus 10 being placed in position in a poured concrete slab C. The present apparatus includes a reusable first or outer container or bucket 12 with one or more smaller second or inner containers or molds 14 removably placed therein. While there may be times when only a single specimen is desired, and thus only one container or mold 14 need be placed within the outer container 12, the outer container 12 is preferably sized so as to contain a plurality of the smaller inner containers 14, preferably on the order of three such smaller containers 14 distributed about the center of the outer container 12.

Figure 2:
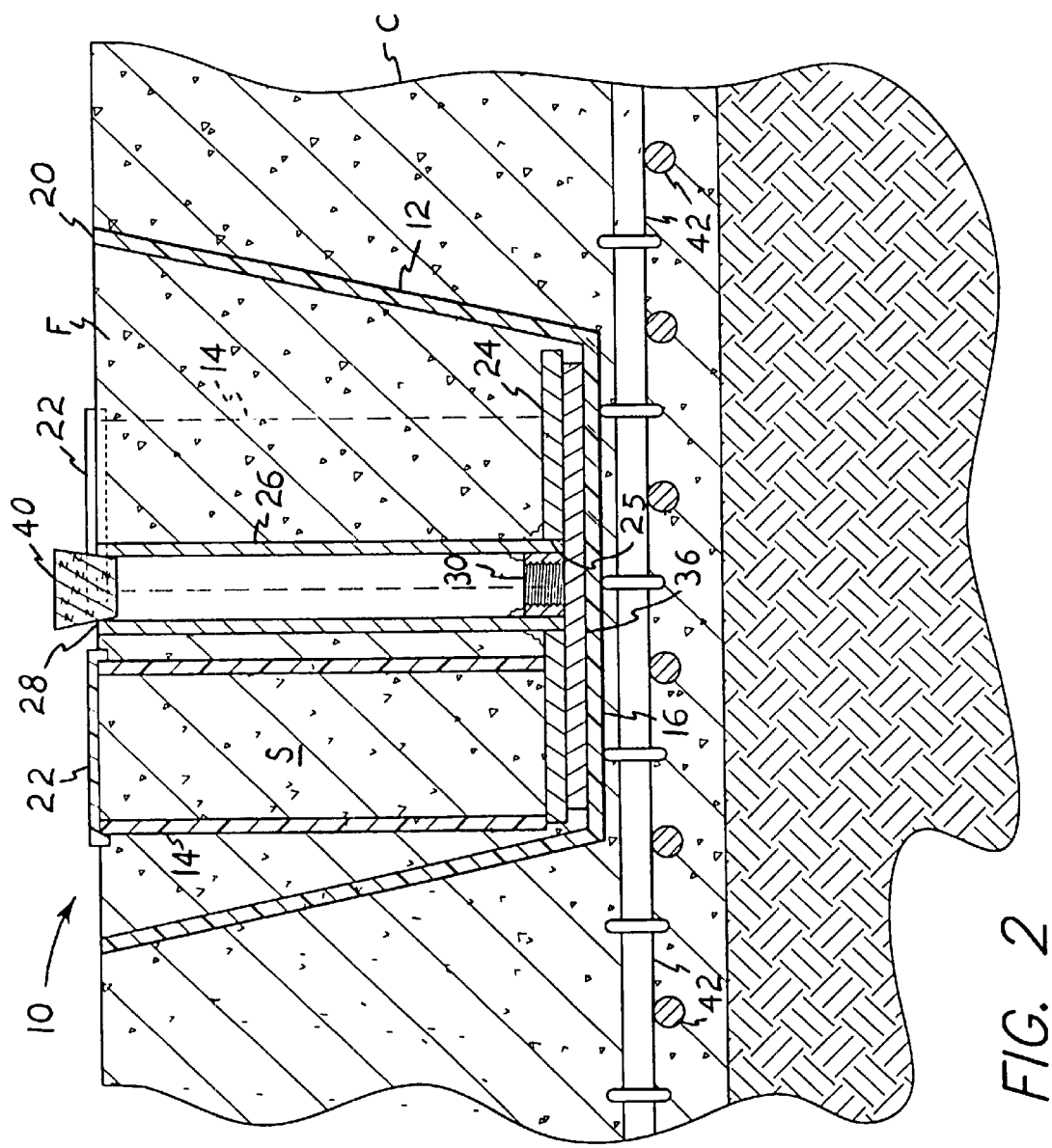
FIG. 2 is a side elevation view in section of the apparatus seated in a poured slab and filled with concrete for curing.
Figure 3:
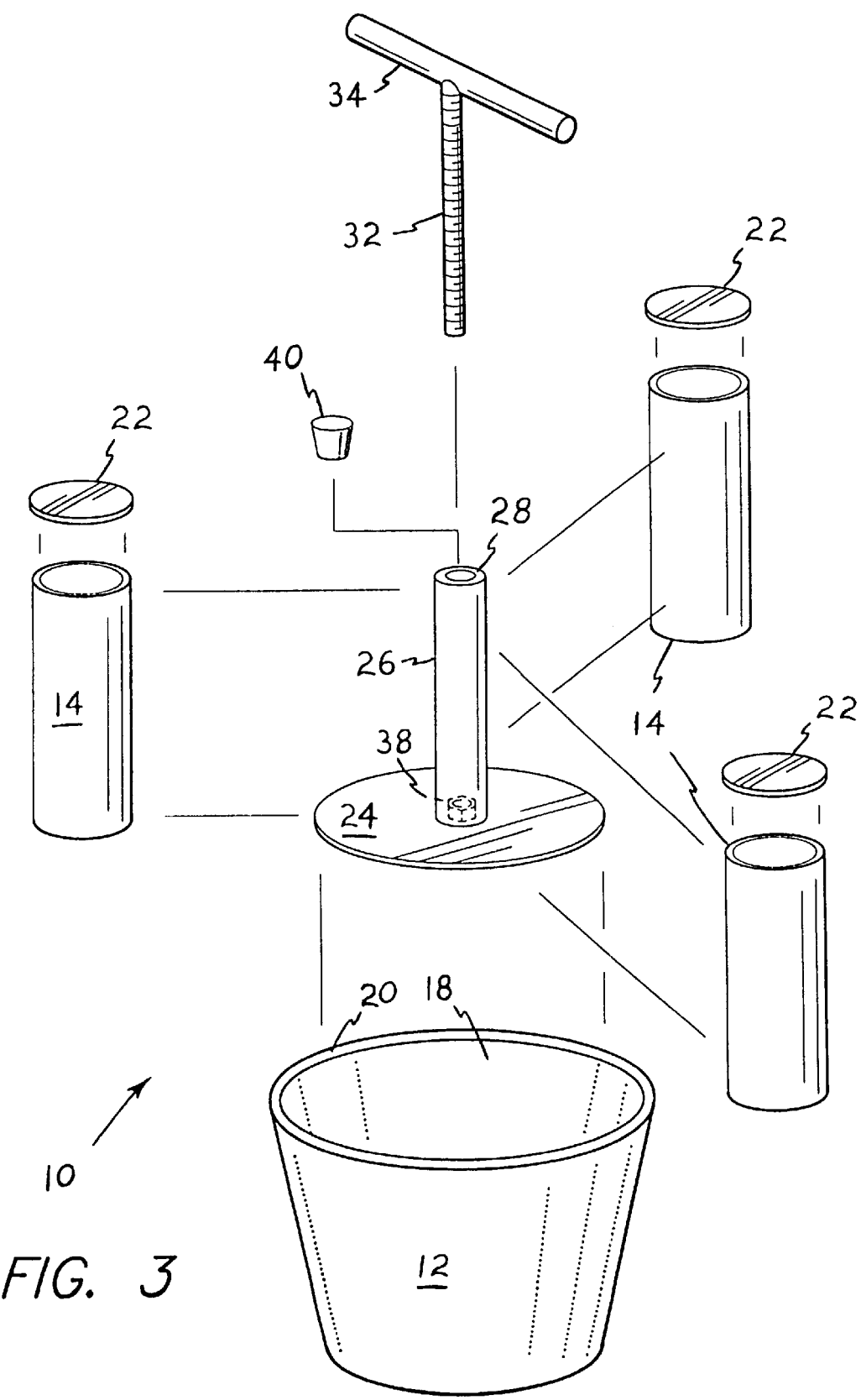
FIG. 3 is an exploded perspective view of the components forming the present concrete test specimen apparatus.

The outer container 12 has a closed bottom 16 and an open top 18 with an upper peripheral edge 20, as shown in FIGS. 2 and 3 of the drawings. The outer container 12 is formed and constructed of a material and in a manner providing for removal from the concrete in which it is placed, after that concrete has cured. Preferably, the outer container 12 is formed of a flexible and resilient material, such as a natural or synthetic rubber or the like, flexible plastic, etc. The outer container 12 is preferably slightly tapered, having a truncated conical shape with a narrower bottom portion, as shown in FIGS. 2 and 3, to provide for ease of withdrawal from the depression in the concrete slab C after the concrete has cured. This results in a similarly shaped void and correspondingly shaped plug for filling the void, which is desired as compression applied to such a tapered, plug shaped fill (as by a vehicle driving over the plug) cannot dislodge the plug through the bottom of the slab, as may occur with a cylindrical fill.

Figure 5:
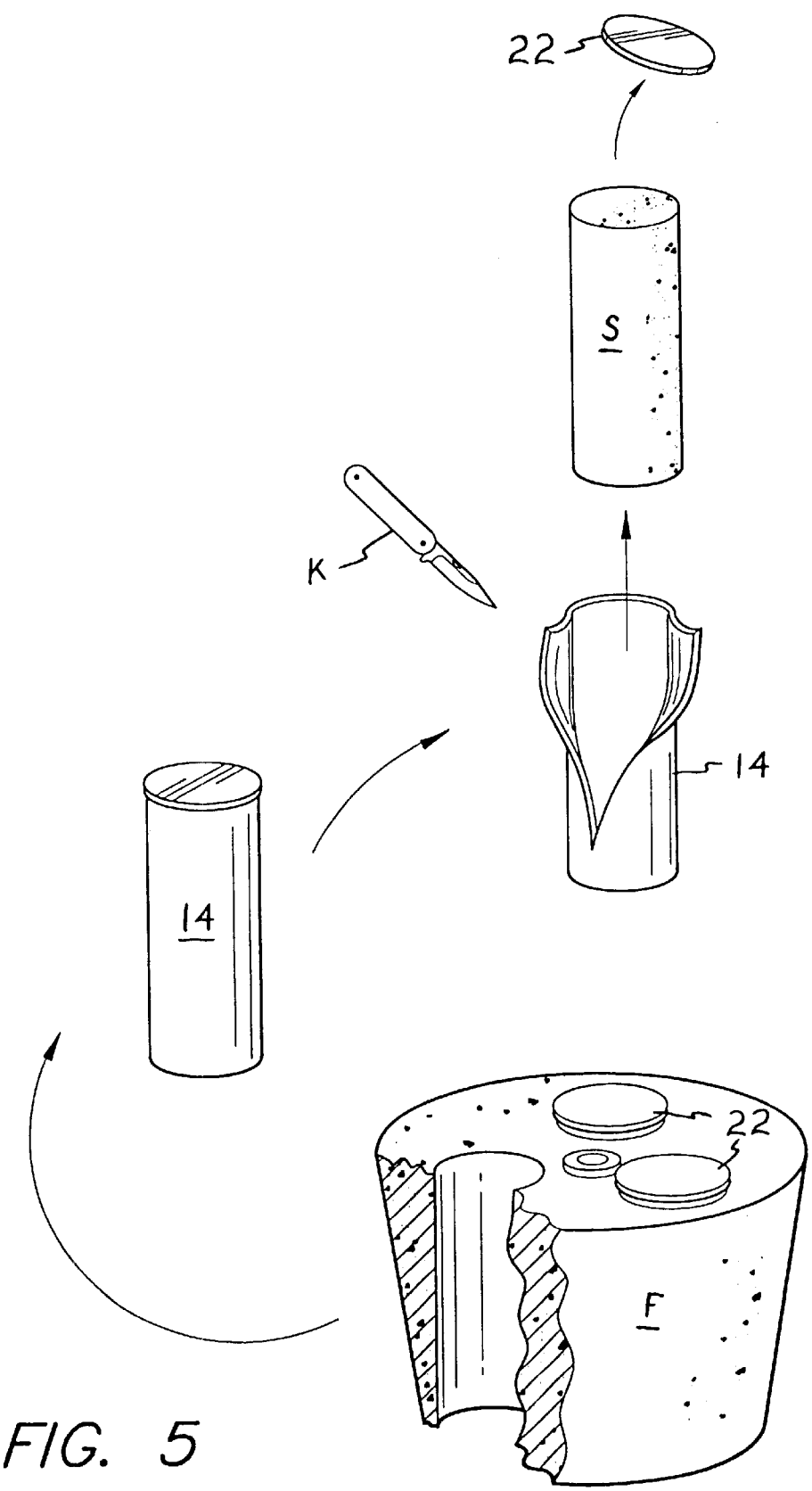
FIG. 5 is an exploded perspective view showing the procedure for removing the test specimens from their individual containers.

The cylindrical inner containers 14 are preferably formed of a relatively thin and inexpensive plastic material, for economical disposal during use of the present invention. An inexpensive plastic material has been found to work well, as it does not interact with the concrete during the curing process. The inner containers 14 are used as molds to cast or form the concrete test specimens S (one of which is shown in FIG. 5), and are sized to conform to the ASTM standards for concrete test specimens for compressive testing. The containers or molds 14 have closed bottoms and open tops which may be removably sealed by caps 22. The inner containers or molds 14 are preferably six inches in interior height, with an interior diameter of three inches for an aspect ratio of 2:1, in order to comply with the preferred range of ASTM test specimen configurations and preclude any requirement for the application of correction factors for non-standard aspect ratios. Other sizes and dimensions may be used if required, according to any specific test requirements.

Figure 4:
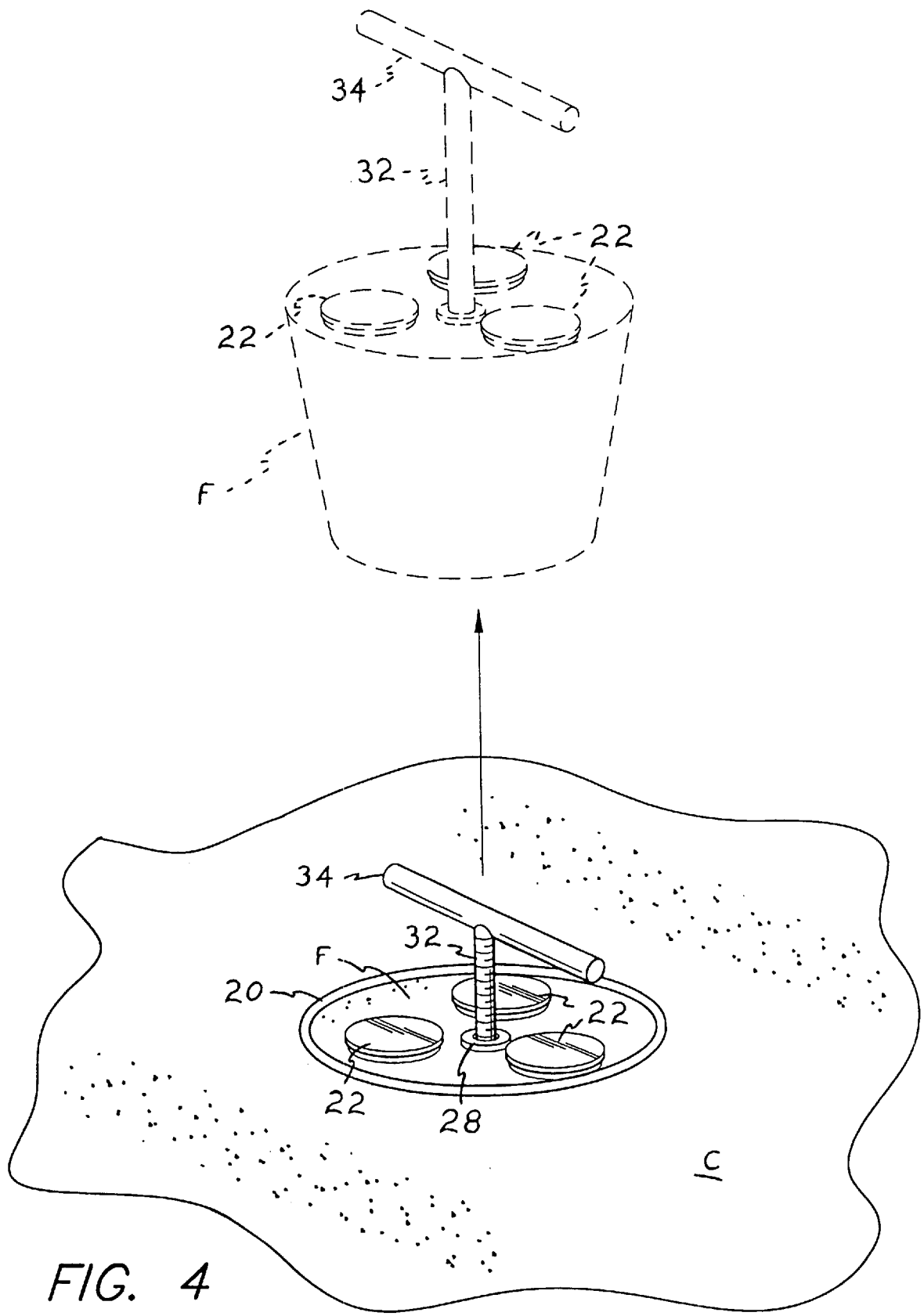
FIG. 4 is a perspective view showing the procedure for removing the test specimens from the cured concrete.

An inner container jacking or removal assembly is placed into the outer container 12 before placing the smaller inner containers 14 into the outer container 12. The jacking or lifting assembly provides means for removing the inner containers 14 from the outer container 12, after the concrete therein has cured. The lifting assembly is shown in FIGS. 2 and 3, and comprises a heavy, rigid base plate 24 (e.g., steel, etc.) having a hole 25 formed (punched, drilled, etc.) in the center thereof. A hollow pipe 26 having an outer diameter sized to fit within the hole 25 (or in other words, the hole 25 may be sized to fit the diameter of the pipe 26 being used) is inserted into the hole 25 and securely attached and sealed (e.g., welded, etc.) to the center of the base plate 24 to extend upwardly therefrom. The pipe 26 is cut to length so that its upper end 28 is substantially level with (or extends only very slightly above) the upper edge 20 of the container or bucket 12 when the lifting assembly is set therein, as shown in FIG. 4.

A nut 30 is welded in the bottom end of the pipe 26 at its juncture with the base or jacking plate 24. While welding a nut 30 into the bottom end of the pipe 26 is preferred in order to provide good grip length for the threaded area, other means of providing a threaded passage through the base plate 24 may be provided such as forming a smaller threaded hole through the bottom of the plate 24, with the pipe 26 abutting the plate 24. A threaded rod 32 (FIGS. 3 and 4) is inserted into the nut 30 or threaded hole to withdraw the plate 24. The smaller specimen container(s) 14 and cured concrete filler F within the container 12 rest atop the plate 24 being withdrawn from the larger container 12, along with the plate 24. The rod 32 preferably has a handle 34 for use in threading the rod 32 into the nut 30 or threads at the bottom of the pipe 26.

A protective bearing plate 36 is placed in the bottom of the container 12, against which the distal end of the threaded jacking rod 32 bears. The bearing plate 36 also precludes penetration of the bottom 16 of the outer container or bucket 12 by the end of the threaded rod 32. This separate bearing plate 36 enables the concrete fill F and its specimens S to be broken loose easily from the interior of the bucket 12, merely by threading the rod 32 through the nut 30 or threaded hole in the bottom of the pipe 26 or jacking plate 24. As the rod 32 is progressively threaded through the nut 30 or threaded passage, its distal end will extend past the bottom of the jacking plate 24 to bear against the underlying bearing plate 36, thus forcing the jacking plate 24 outwardly from the void with the concrete fill F and specimens S resting thereon.

The above described threaded passage through the bottom of the jacking plate 24 and separate bearing plate 36 placed therebeneath, is preferred for facilitating the removal of the cured concrete fill F from the bucket or container 12, as the lifting force developed by the screw jack principle is more than sufficient to lift the fill F and specimens S from the container 12 without undue effort on the part of the worker involved. However, it will be seen that other means of accomplishing the retrieval of the specimens S may be provided, if so desired. Alternatively, a threaded insert 38 (nut, etc.) may be affixed (welded, etc.) in the lower end of the pipe 26 before welding the pipe 26 to the plate 24, as shown in the alternative embodiment of FIG. 3 of the drawings, thus obviating any requirement for the additional protective plate 36.

However, it will be understood that this is not a preferred means of extracting the concrete fill F and specimens S from the container 12, due to the adhesion of the fill F within the container 12 and the mass of the fill F, specimens S, and associated extraction components (plate 24, pipe 26, etc.). The extractive force required is considerable, and it is unlikely that the average worker would be able to develop sufficient force to extract the concrete fill F from the container 12 without using some means (i.e., the rod 32 bearing against the underlying bearing plate 36, as shown in FIG. 2 of the drawings) to break loose the fill F from the interior of the bucket or container 12.

Once the concrete has cured and the plate assembly with its specimen container(s) 14 and hardened concrete outer container filler F have been removed from the outer container 12, the filler F is broken apart to retrieve the specimen container(s) 14 and recover the plate assembly, generally as illustrated in FIGS. 4 and 5 of the drawings. Each of the capped containers 14, with its cured concrete test specimen S contained therein, is sent to a testing facility for compressive testing of the specimens S. The specimens are easily removed from their respective containers 14 as shown in FIG. 5 of the drawings, by removing the caps 22 and cutting open (e.g., knife K or other tool) or otherwise removing the containers 14 from their respective specimens S. The specimens are then ready for testing.

Figure 6:
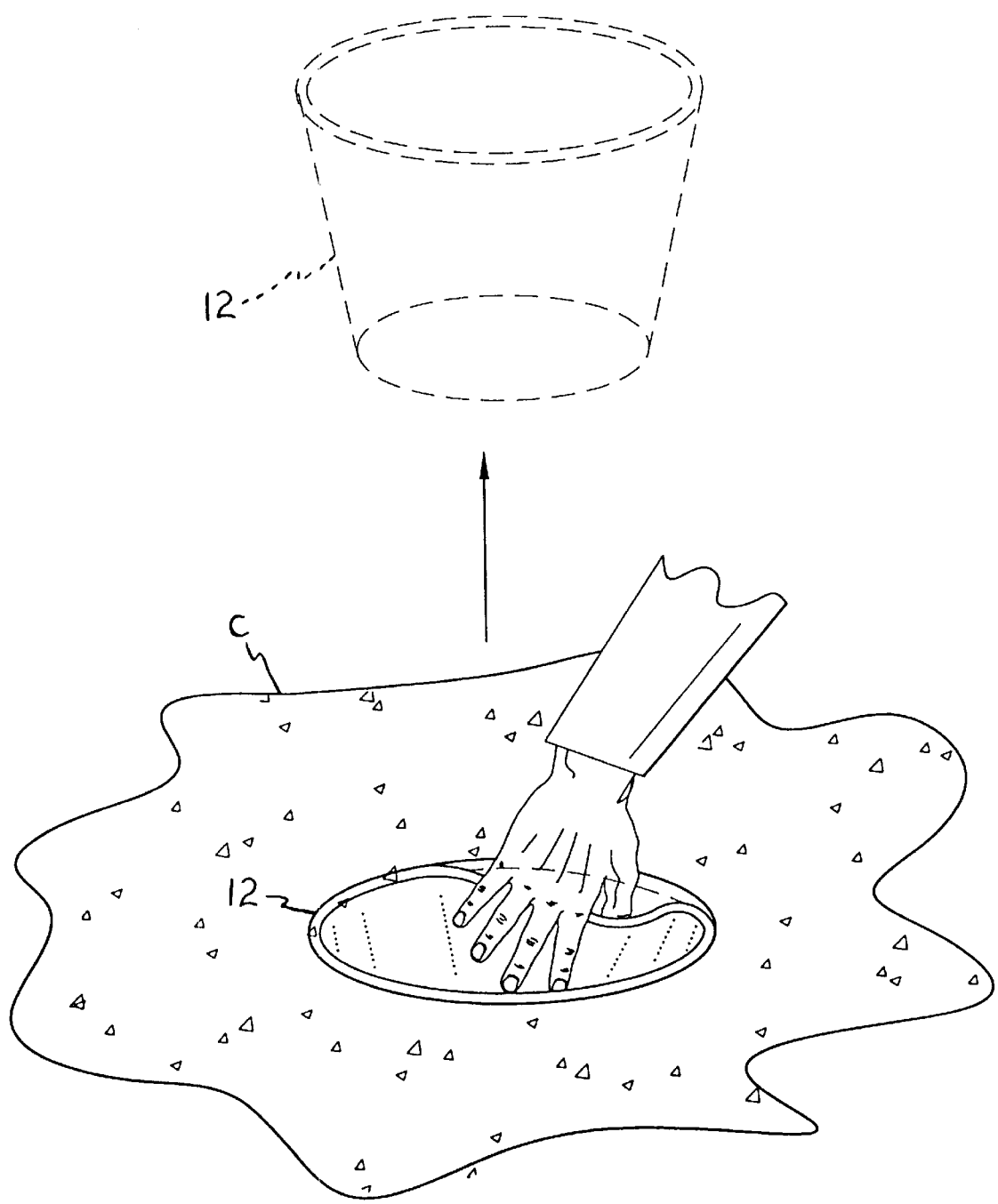
FIG. 6 is a perspective view showing the procedure for removing the outer container from the cured concrete slab.

Once the inner containers 14 have been broken loose from the cured concrete fill F which was removed from the outer container 12, the lifting assembly is removed for reuse as desired. Also, after the cured concrete fill F is removed from the imbedded outer container 12, the outer container 12 may be removed from its location in the concrete slab C for reuse. The flexible nature of the rubber or other flexible, resilient material from which the outer container 12 is formed, enables it to be flexed inwardly to break it loose from the surrounding concrete slab C, and lifted from the depression in the slab C, as shown in FIG. 6 of the drawings. The resulting hole or depression in the slab C is then filled with fresh concrete and leveled with the surrounding slab C to complete the work.

Figure 7:
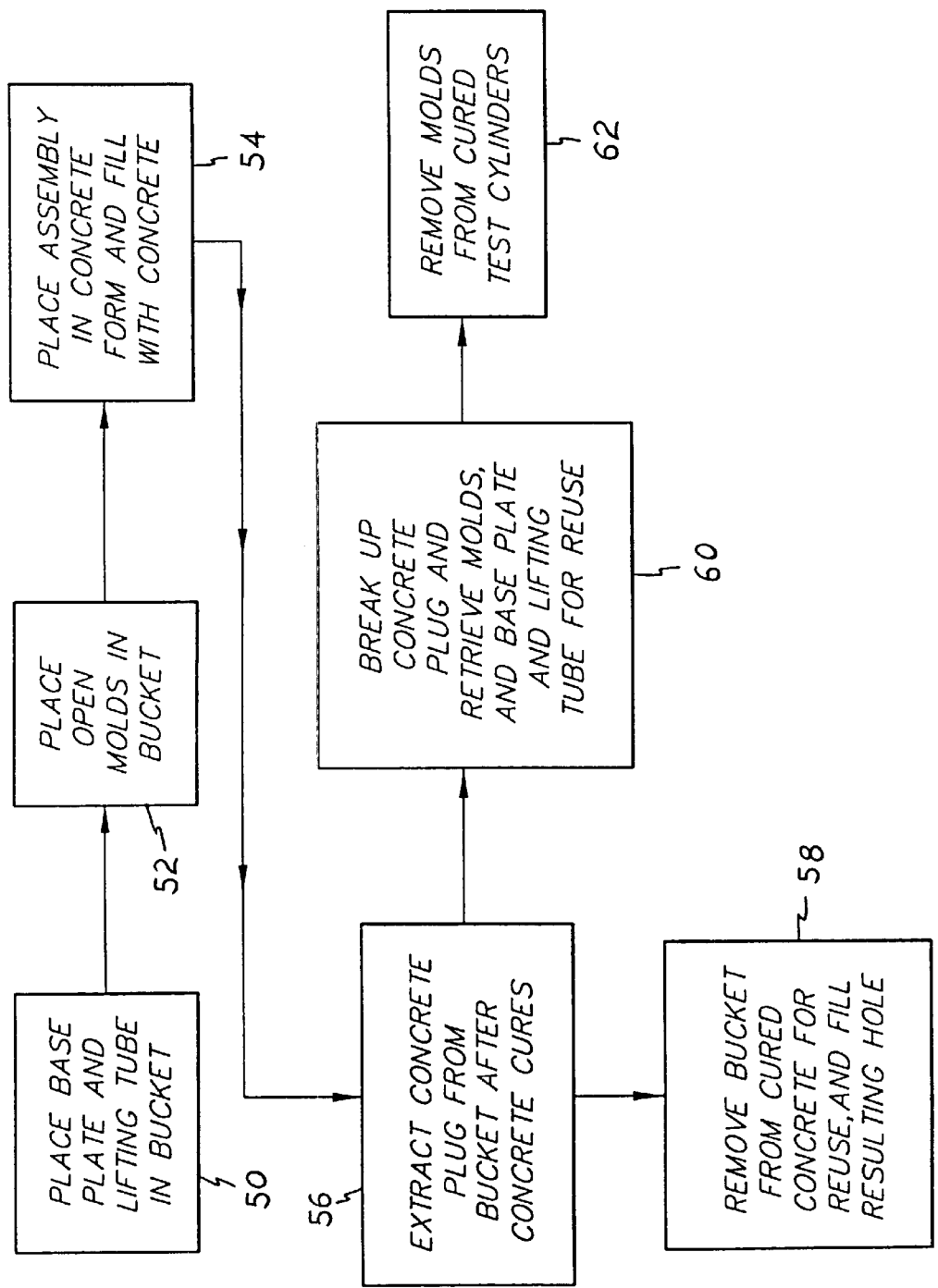
FIG. 7 is a flow chart showing the general steps in the method of forming test specimens using the present apparatus.

FIG. 7 serves to summarize the steps in the method or process associated with the use of the present reusable test specimen apparatus 10. First, the lifting assembly, comprising the bearing plate 36, base plate 24, and lifting tube or pipe 26, is placed into the outer container or bucket 12, generally as indicated by the first step 50 of FIG. 7. The lifting rod 32 is removed from the lifting assembly, and the upper end 28 of the pipe 26 is capped with some form of removable closure means 40 (e.g., cork or other stopper, as shown in FIGS. 2 and 3) to plug the upper end 28 of the pipe 26 and preclude the entry of wet concrete therein. The opened (i.e., caps 22 are removed) inner containers or molds 14 are then placed within the outer container or bucket 12, generally as shown in the second step 52 of FIG. 7.

The apparatus 10 may be placed in various locations as desired within an area before the concrete is poured, or may alternatively be set into the poured but fresh or wet concrete slab C after pouring, by digging out a depression in the concrete C and setting the assembly 10 into the depression. In the event that the slab C is somewhat thicker than the height of the outer container 12 and its inner container(s) 14, the outer container 12 may be raised so that its upper edge 20 is level with the top T or upper surface of the slab C by installing a grid of reinforcing bars 42 (rebar) or other suitable support means (screen, etc.) within the concrete at an appropriate depth below the upper surface, beneath the apparatus 10 before it is placed in the depression formed in the slab, or before placing the apparatus in the concrete form before pouring.

Alternatively, the density and viscosity of wet concrete enables the container 12, with its extraction assembly and specimen containers therein, to be "floated" in freshly poured concrete when filled with like concrete, with its rim essentially flush with the upper surface of the concrete, essentially as shown in FIG. 1 of the drawings. The remaining space around the outer container 12, as well as the inner container(s) 14 and the space between the inner container(s) 14 and outer container 12, is then refilled with the wet concrete which was removed from the poured slab to form the depression for the apparatus 10, and the cap(s) 22 is/are placed over the top(s) of the inner container(s) 14 to stabilize the cylindrical shape(s) of the upper end(s) of the container (s) 14 and to seal the specimen(s) therein during curing, generally as indicated by the third step 54 of FIG. 7.

At this point, the concrete of the slab C (and of course the concrete within the inner and outer containers 14 and 14 of the present apparatus) is left to cure, with the same curing conditions occurring in the test specimens within the inner container(s) 14 as occur throughout the remainder of the slab C. The latent heat developed by the curing concrete extends throughout the slab C, including through the outer and inner containers 12 and 14, thus subjecting the concrete within those containers 12 and 14 to identical curing temperatures as those experienced throughout the remainder of the slab in the area where the apparatus 10 was placed.

Once the concrete slab C has cured or hardened, the lifting assembly, with its concrete plug or filler F and encapsulated inner container(s) 14, is removed from the outer container 12, as noted by the fourth step 56 of FIG. 7. This is achieved by removing the closure 40 from the upper end 28 of the lifting pipe 26, inserting the jacking rod 32 therein, and threading the jacking rod 32 into the mating threaded passage (nut 30 in the bottom end of the pipe 26, or other threaded insert 38, etc.). The entire lifting assembly with its concrete plug or filler F is then lifted from the outer container or bucket 12, which remains temporarily captured within the hole or depression in the slab C. Once access has been gained to the outer container 12 and the contact or bearing plate 36 therein, they are easily removed from the cured slab C by flexing the container 12 inwardly, as shown in FIG. 6 and indicated by the fifth step 58 of FIG. 7. The resulting hole is then filled with fresh concrete and finished to the level of the slab C, as indicated generally in the fifth step 58 of FIG. 7.

The concrete plug or filler F removed from the outer container 12 is then broken up to access the lifting assembly for reuse, and also to access the inner container(s) or mold(s) (preferably three, for reasons described further above) containing the concrete test specimen(s), as indicated by the sixth step 60 of FIG. 7. The test specimen(s) is/are then sent to an appropriate test facility, where the container(s) is/are removed from their respective cured specimen(s) for testing, generally as illustrated in FIG. 5 of the drawings and described in the seventh step 62 of FIG. 7.

In summary, the present method and apparatus for producing concrete test specimens provides not only more accurate specimens, but also a more economical means of producing such specimens. The test specimens themselves cure in situ, in exactly the same concrete slab in which they were poured and under exactly the same conditions of heat, weather, and other factors which affect the strength of cured concrete. The continuous concrete fill completely surrounding the apparatus, being devoid of any air gaps or channels between various components, precludes any insulation effects from such air gaps between the slab and the test specimens curing therein.

Moreover, the ability of most of the components comprising the present apparatus to be reused, greatly reduces the cost of forming cylindrical test specimens, particularly for a relatively large structure. With test apparatus in which much of the device remained captured within the cured concrete slab, the cost of such lost equipment is not a small consideration in the cost of the project. Using the present invention, the only non-reusable components are the one or more inner containers or molds used to cast the actual test specimens. As a result, the concrete industry may now enjoy the results of a device and method which accurately duplicates the actual in place concrete strength, as well as an economical means for obtaining the representative test data.

It is to be understood that the present invention is not limited to the embodiments described above, but encompasses any and all embodiments within the scope of the following claims.

We claim:

1. A reusable apparatus for in situ forming of concrete test specimens, comprising:

a flexible, reusable outer container having a closed bottom and an open top with an upper peripheral edge, said outer container adapted for placing in a slab of wet concrete and filling with wet concrete;

at least one inner container removably disposed within said outer container and adapted for filling with a representative specimen of said wet concrete; and a lifting assembly for removing said at least one inner container from said outer container, said lifting assembly including a heavy, rigid base plate removably placed within said outer container and beneath said at least one inner container;

a hollow pipe having a lower end secured concentrically to said base plate and extending upwardly therefrom;

said hollow pipe having an upper end substantially level with said upper peripheral edge of said outer container when said base plate is placed directly upon the bottom of said outer container;

a threaded passage disposed in said hollow pipe; and a threaded rod for inserting through said pipe for engaging said threaded passage of said lifting assembly, for lifting said lifting assembly and said at least one inner container from said outer container after the concrete has cured.

2. The apparatus according to claim 1, further including:

a plurality of inner containers.

3. The apparatus according to claim 1, further including:
means for removably sealing the concrete specimen within said at least one inner container.

4. The apparatus according to claim 1, further including:
means for placing said upper edge of said outer container level with the upper surface of the poured concrete slab.

5. The apparatus according to claim 1, wherein:
said base plate includes a concentric passage therethrough;
said lower end of said pipe is secured within said passage of said base plate;
said threaded passage comprises a threaded insert disposed within said lower end of said pipe; and
a bearing plate disposed between said base plate and said bottom of said outer container, for applying jacking pressure thereto by means of said threaded rod for extracting said lifting assembly from said outer container.

6. The apparatus according to claim 1, wherein:
said base plate is devoid of any passage therethrough;
said lower end of said pipe is secured concentrically to said base plate; and
said threaded passage comprises a threaded insert disposed within said lower end of said pipe.

7. The apparatus according to claim 1, further including:
removable closure means for said upper end of said pipe for precluding entry of wet concrete therein during pouring.

8. The apparatus according to claim 1, wherein:
said at least one inner container comprises a cylinder having an interior height of substantially six inches and an interior diameter of substantially three inches.

9. The apparatus according to claim 4, wherein said means for placing said upper edge of said outer container level with the upper surface of the poured concrete slab comprises:
at least one support means disposed beneath said outer container; and
said at least one support means being positioned so that said upper peripheral edge of said outer container is disposed substantially level with the upper surface of the concrete slab.

10. A method for forming concrete test specimens in situ in a poured concrete slab, comprising the following steps:
(a) providing a flexible, reusable outer container having a closed bottom and an open top with an upper peripheral edge;
(b) further providing at least one inner container for removably placing within the outer container;
(c) further providing reusable extraction means for removing the at least one inner container from the outer container after the concrete has cured;
(d) placing the extraction means within the outer container, and placing the at least one inner container upon the extraction means;
(e) placing the outer container, extraction means, and at least one inner container within the wet concrete of the slab;
(f) filling the outer container and the at least one inner container with wet concrete of the same batch as that of the surrounding slab;
(g) curing the concrete of the slab and within the outer container and at least one inner container;
(h) extracting the at least one inner container from the outer container by the extraction means;
(i) removing the reusable outer container from the concrete slab;
(j) breaking up the concrete surrounding the at least one inner container, and retrieving the at least one inner container and extraction means; and
(k) removing the cured concrete specimen from the at least one inner container, for testing.

11. The method for forming concrete test specimens according to the method of claim 10, further including the step of providing means for placing the upper edge of the outer container level with the upper surface of the poured concrete slab.

12. The method for forming concrete test specimens according to the method of claim 10, further including the steps of:
(a) providing a plurality of inner containers; and
(b) filling each of the inner containers with concrete, and forming a plurality of concrete test specimens thereby.

13. The method for forming concrete test specimens according to the method of claim 10, further including the step of removably sealing the concrete specimen within the at least one inner container.

14. The method for forming concrete test specimens according to the method of claim 10, further including the steps of:
(a) forming the lifting means using a heavy, rigid base plate;
(b) securely attaching and sealing a hollow pipe generally perpendicularly to the base plate and extending upwardly therefrom;
(c) forming the upper end of the pipe to be level with the upper peripheral edge of the outer container when the base plate is placed within the outer container;
(d) forming a threaded passage within the lifting assembly;
(e) providing a threaded rod;
(f) inserting the rod through the pipe and engaging the threaded passage; and
(g) extracting the base plate and at least one inner container from the outer container, by means of the threaded rod.

15. The method for forming concrete test specimens according to the method of claim 14, wherein the step of forming a threaded passage in the lifting assembly further includes the steps of:
(a) forming a central hole in the base plate;
(b) securing the lower end of the pipe within the hole in the base plate; and
(c) installing a threaded insert within the lower end of the pipe.

16. The method for forming concrete test specimens according to the method of claim 14, wherein the step of forming a threaded passage in the lifting assembly further includes the steps of:
(a) installing a threaded insert within the lower end of the pipe; and
(b) securing the lower end of the pipe concentrically to the top of the base plate.

17. The method for forming concrete test specimens according to the method of claim 14, wherein the step of placing the outer container, lifting means, and at least one inner container within the wet concrete of the slab, further includes the steps of:
(a) providing removable closure means for the upper end of the pipe; and (b) removably installing the closure means in the upper end of the pipe for precluding entry of wet concrete therein during pouring.

18. The method for forming concrete test specimens according to the method of claim 10, further including the step of forming the at least one inner container as a cylinder having an interior height of substantially six inches and an interior diameter of substantially three inches.

19. The method for forming concrete test specimens according to the method of claim 11, wherein the step of providing means for placing the upper edge of the outer container level with the upper surface of the poured concrete slab further includes the steps of:

(a) providing at least one support means;

(b) positioning the support means within the wet concrete so that the upper peripheral edge of the outer container is disposed substantially level with the upper surface of the concrete slab, when the outer container is placed upon the support means.

* * * * *